| United States Patent [19] | [11] | 4,310,504 |
|---|---|---|
| Derfler et al. | [45] | Jan. 12, 1982 |

[54] DRY RADIOIMMUNOASSAY TEST COMPOSITION CONTAINING STABILIZED LABEL/ANTIBODY MIXTURE

[75] Inventors: Sara Derfler; Yehuday Tamir, both of Jerusalem, Israel; Daniel B. Wagner, Raleigh, N.C.

[73] Assignee: Ames-Yissum Ltd., Jerusalem, Israel

[21] Appl. No.: 75,060

[22] Filed: Sep. 12, 1979

[30] Foreign Application Priority Data

Sep. 13, 1978 [IL] Israel .................................... 55564

[51] Int. Cl.$^3$ ...................... G01N 33/48; G01T 1/00; B65D 71/00
[52] U.S. Cl. ..................................... 424/1; 23/230 B; 422/61; 424/12
[58] Field of Search ............................ 424/1, 1.5, 12; 23/230 B; 422/61

[56] References Cited

U.S. PATENT DOCUMENTS 4,017,597 4/1977 Reynolds .............................. 424/1.5

Primary Examiner—Benjamin R. Padgett
Assistant Examiner—Christine M. Nucker
Attorney, Agent, or Firm—Andrew L. Klawitter

[57] ABSTRACT

A dry radioimmunoassay test composition comprising a mixture of a radiolabelled form of a ligand, i.e., a hapten or an antigen, an antibody for the ligand, and a heavy metal cation, e.g., cupric ion, to inhibit the complex-forming reaction between the radiolabelled ligand and the antibody. A method for preparing the dry test composition is also provided. In use in a radioimmunoassay, the dry test composition is reconstituted with an aqueous liquid and combined with a test sample and a chelating agent to bind the heavy metal cation, permitting reaction among any ligand present in the sample, the radiolabelled ligand, and the antibody. A test kit for performing such radioimmunoassay is also provided.

19 Claims, No Drawings

DRY RADIOIMMUNOASSAY TEST COMPOSITION CONTAINING STABILIZED LABEL/ANTIBODY MIXTURE

BACKGROUND OF THE INVENTION

1. Field of the Invention

The present invention relates to an improved test composition for use in radioimmunoassays for the determination of haptens and antigens (hereinafter referred to as "ligands") in liquid samples including body fluids such as serum. The invention also concerns a method for preparing such test composition and an improved radioimmunoassay method and test kit.

Radioimmunoassay methods, in general, are based on the competition between a specific native ligand, the amount of which is to be determined in a sample, and a known amount of the same ligand in radioactively labelled form, for a limited number of available binding sites on an antibody which is specific towards the ligand under assay. Thus, in a system consisting of an unknown amount of unlabelled native ligand, a known amount of a radioactively labelled ligand and a limited known amount of antibody, the greater the concentration of unlabelled native ligand from the sample, the less the labelled ligand will be bound by the antibody.

If the concentration of labelled ligand and antibody is fixed and the only variable is the level of unlabelled ligand, it becomes possible to establish an assay system for measuring the unknown level of unlabelled ligand, by separating the ligand-antibody complex (the "bound" species) from the remaining free ligand (both labelled and unlabelled—the "free" species). The radioactivity of the unknown is compared with the values given by a range of known amounts of the ligand treated in the same manner. The values obtained from the determination of the standard samples may be used for establishing a standard calibration curve for the specific system and this curve may then be used to determine an unknown concentration of the ligand in an unknown sample.

There are many procedures for separating the ligand-antibody complex from the free unbound ligand, amongst which chromatoelectrophoresis, ascending paper-wick chromatography, precipitation by salts, organic materials or solvents, selective adsorption on various so-called "immunosorbents," either in suspension or on chromatographic columns, and ion exchange techniques may be mentioned as examples of such procedures and reference is made to the detailed discussions of these known methods in U.S. patent application Ser. No. 852,105, incorporated herein by reference filed Nov. 16, 1977 and assigned to the instant assignee.

The first step of most current immunoassay procedures involves the preparation of an incubation mixture (or reaction mixture) including a known quantity of the ligand under assay in radioactively labelled form, a known volume of the sample (i.e., an aqueous solution of the ligand under assay in native form), and a predetermined quantity of the specific binder for said ligand, which, as a rule, is an antibody. This reaction mixture is then incubated for a suitable time to cause a reaction between the ligand and the specific binder therefor so that a part of the ligand forms a ligand-binder complex. The preparation of this reaction mixture involves the dispensing of predetermined volumes of at least three different solutions and in many cases the number is even greater, e.g., when a buffer solution has to be added. Furthermore, in most clinical radioimmunoassays where the sample is a body liquid taken from a patient, the volumes involved are very small which renders their accurate measurement and dispensing a rather delicate and complicated task. It is thus easy to understand why the accuracy of radioimmunoassay methods is comparatively low, some of the major sources of inaccuracy being the errors in the micro-dispensing of the solutions of the components of the reaction mixture.

2. Description of the Prior Art

In order to increase the accuracy of radioimmunoassay methods as well as the shorten and simplify the experimental procedure performed by the medical laboratory technicians, it has been proposed to prepare the reaction mixture (or incubation mixture) in vessels already containing the required pre-measured amount of either the radioactively labelled ligand under assay or the specific binder therefor. Kits for specific immunoassay determinations comprising a number of test tubes each containing a pre-measured quantity of either of the above-mentioned components are commercially available. For better storage stability and convenient transportation, the test tubes in these kits contain the radioimmunoassay component in lyophilized form and the kit usually includes also a suitable buffer solution for dissolving (reconstituting) the lyophilized component in the test tubes before the other reactants are added. Although the amount of buffer solution, used for the reconstitution of the lyophilized component in the test tube, does not have to be measured with a high degree of accuracy, the use of kits of this type still requires the accurate measurement, usually by pipetting, of at least two solutions by the medical laboratory technician. Thus, if the lyophilized component in the test tubes is the radioactively labelled ligand, it is necessary to add, in addition to the above-mentioned buffer solution, accurate amounts of both the specific binder and of the sample to be assayed.

Some suggestion has been made to lyophilize both the radiolabelled ligand and the binder in the same container as exemplified by the disclosures in U.S. Pat. No. 4,017,597; British Pat. No. 1,411,381 and Belgian Pat. No. 852,990. However, the hitherto disclosed methods require careful layering of the radiolabeled ligand and the binder or instantaneous freezing of a mixture with no assurance that some complexing between the labelled ligand and the binder does not take place during the preparative process, during storage, or after reconstitution but before addition of the sample.

U.S. Pat. No. 4,107,284 discloses a stabilized radioimmunoassay reagent wherein the radiolabelled ligand and the binder are in the form of their complex. Upon reconstitution and use in an assay, a substantial incubation time will be required to permit dissociation for competition between labelled ligand and sample or native ligand.

Thus, there is a need for developing a stabilized, dry radioimmunoassay reagent wherein the labelled ligand and the antibody are not bound in the form of their complex. Such a reagent would provide a single reagent for introducing both the label and the antibody to the reaction mixture in their free, or non-complexed, forms.

SUMMARY OF THE INVENTION

It is an object of the present invention to provide a radioimmunoassay method which is more accurate and, at the same time, simpler to perform in the medical laboratory. In attaining this object the invention makes use of the unexpected finding that it is possible to prepare lyophilized mixtures of a radioactively labelled ligand and a specific antibody therefor in the same vessel, without any immunological reaction occurring between them, provided that the mixture comprises an effective amount of a heavy metal cation capable of inhibiting the complex-forming reaction between the antibody and the ligand. It has further been found, in accordance with the present invention, that the ligand-antibody system can be reactivated, after the sample and a suitable buffer solution have been added thereto, by means of a strong chelating agent capable of forming a stable complex with said heavy metal cation.

Accordingly, the present method provides a dry, usually lyophilized, radioimmunoassay test composition comprising a mixture of a radiolabelled form of a ligand selected from haptens and antigens, an antibody for the ligand, and a heavy metal cation, usually cupric ion, in an amount sufficient to inhibit substantially the complex-forming reaction between the radiolabelled ligand and the antibody during storage and upon reconstitution with a predetermined volume of an aqueous liquid (e.g., upon reconstitution for use in an assay). Such dry test composition is conveniently obtained by:

(a) preparing an aqueous liquid mixture of the radiolabelled ligand, the antibody, and the heavy metal cation present in an amount sufficient to inhibit substantially the complex-forming reaction between the radiolabelled ligand and the antibody; and (b) drying said liquid mixture, preferably by lyophilization.

The test composition of the present invention is used in a radioimmunoassay by performing the steps of:

(a) reconstituting said composition with a predetermined volume of an aqueous liquid, (b) combining the reconstituted liquid composition, either sequentially or simultaneously, with the liquid sample and with a chelating agent for the heavy metal cation in an amount sufficient to bind substantially all of the cation present, (c) incubating the resulting liquid reaction mixture, (d) separating the fraction of the radiolabelled ligand which becomes bound to the antibody during the incubation period from that which does not become so bound, and (e) measuring the radioactivity of one of the separated fractions as a function of the presence or amount of the ligand in the liquid sample.

Any heavy metal cation, or an equivalent thereof, which substantially inhibits the ligand-antibody reaction involved may be used. Numerous such materials are known in the literature and the art. Corresponding chelating agents likewise will be evident to one working in the field. Where the heavy metal cation is cupric ion, the preferred chelating agent is ethylenediamine tetraacetic acid.

The radioimmunoassay is conveniently performed with the use of a test kit comprising, in a packaged combination, (a) a container holding the dry test composition of the present invention, and (b) a container holding a chelating agent for the heavy metal cation.

DESCRIPTION OF THE PREFERRED EMBODIMENTS

In the first step of the method for preparing the test composition, a known volume of an aqueous liquid mixture, usually a buffer solution, is prepared to include the radioactively labelled ligand, the specific antibody for the ligand and at least one heavy metal cation in an amount sufficient to inhibit the complex-forming reaction between the antibody and the ligand. Alternatively, the heavy metal cation (or cations) may be dissolved first in an aqueous solution containing the specific antibody, and the resulting combined solution admixed with the aqueous solution of the radioactively labelled ligand. In this procedure it has been found advantageous to allow the mixture of the antibody with the heavy metal cation to stand for some time, preferably more than half an hour, in order to ensure complete inhibition of the antibody by the heavy metal cation, before this solution is admixed with the solution of the radioactively labelled ligand in the vessel.

Lyophilization of the above-mentioned aqueous mixture is carried out in a known manner, by freezing the mixture in the vessel at very low temperature, e.g., at −70° C. or at the temperature of liquid nitrogen, and connecting the vessel to a source of high vacuum. After lyophilization is complete, the vessel and its contents are allowed to reach room temperature, the vessel is disconnected from the source of vacuum and is tightly sealed in order to prevent the entry of water vapour.

The sealed vessels containing the lyophilized mixture of radioactively labelled ligand, specific antibody therefor and heavy metal cation, can be stored for prolonged periods until required for use in the performance of a radioimmunoassay in the medical laboratory. For the performance of the actual assay, it is necessary to add to the lyophilized mixture in the vessel accurately measured volumes of only two solutions, namely, the standard solution or a sample solution containing the ligand under assay and the chelating agent, usually dissolved in a suitable buffer solution, serving to form a stable complex with the heavy metal cation so as to cancel its inhibitory action on the ligand-antibody system. These two solutions can be added simultaneously for example by means of a so-called "diluter-dispenser" apparatus. Alternatively if the two solutions are to be added manually, e.g., by pipetting, it is preferable to add first the solution of the standard or the sample and to allow the lyophilized mixture to completely dissolve therein, before adding the chelating agent. This sequence ensures that the complex-forming reactions between the antibody and the radioactively labelled ligand on the one hand, and the native ligand in the sample on the other hand, will commence simultaneously.

After the required period of incubation at room temperature or another suitable temperature, during which a part of the ligand (both labelled and native) forms a ligand-antibody complex with the specific antibody, the free, unbound ligand is separated from the ligand-antibody complex. To this end, any of the known methods conventional in the radioimmunoassay field can be employed.

In accordance with a preferred embodiment of the invention, the separation of the free ligand from the ligand-antibody complex is carried out by the so-called "ascending chromatography" technique which is described in the aforementioned U.S. patent application Ser. No. 852,105. In accordance with this technique there is dipped into the reaction mixture in the vessel the intake tip of a column filled with an absorbent material capable of absorbing the total amount of reaction mixture in the vessel, which material also preferentially adsorbs either the ligand or the ligand-antibody complex. The absorbent material in the column is allowed to absorb all the liquid in the vessel whereby the preferentially adsorbed component is held in the intake tip region of the column whereas the non-adsorbed component ascends by capillary action in the adsorbent material. The two components become thus separated along said column and the distance between them may be further increased by introducing a further amount of water or aqueous buffer solution through the intake tip of the column and allowing it to be adsorbed by and ascend in the adsorbent material. In accordance with this method the measurement of the radioactivity of the adsorbed component becomes a comparatively simple and straightforward operation involving the selective measurement of the radioactivity of the intake tip region of the column.

It should be clear, however, that the present invention is not limited to the above described method of separating the free ligand from the ligand-antibody complex, and any other suitable method can be used for that separation within the scope of the invention.

In another preferred aspect, the present invention provides, for the performance of the radioimmunoassay method, a test kit comprising at least one sealed vessel containing a lyophilized mixture of a known quantity of the ligand under assay in radioactively labelled form, a known quantity of a specific antibody for said ligand and an effective amount of a heavy metal cation capable of inhibiting the complex-forming reaction between said ligand and said specific antibody therefor. The kit may optionally also include packaged aqueous buffer solution for the dissolution of the lyophilized mixture in the course of the actual radioimmunoassay determination, and this buffer solution may optionally include also the strong chelating agent capable of forming a stable complex with said heavy metal cation. Alternatively a solution of said chelating agent may be included in the kit in a separately packaged form. A further optional component of the kit is packaged native ligand in known amounts which serves for the establishment of a standard curve, as explained above.

In accordance with a preferred embodiment of the invention, there is provided a kit comprising the above-mentioned components and, in addition, at least one column pre-packed with a suitable absorbent material, for separating the free ligand from the ligand-antibody complex by the "ascending chromatography" technique as described hereinabove.

The invention also provides a preferred method for preparing the lyophilized mixture of components contained in the sealed vessels in the aforementioned kits. This method comprises a procedure identical with that in the first two stages of the process of the invention, as specified above, namely the preparation of the mixture and its lyophilization. In accordance with a preferred embodiment of this method, an automatic diluter-dispenser is used for the double dispensing into a series of vessels (e.g., test tubes) of predetermined volumes of two stock solutions, namely an aqueous solution of the radioactively labelled ligand under assay and an aqueous solution of the specific antibody for the ligand (e.g., an antiserum solution) including a sufficient concentration of the heavy metal cation necessary to inhibit the ligand-antibody complex formation reaction. Either or both of these solutions may also include additional components, such as suitable buffer systems, preservatives, fillers and the like.

The invention is further illustrated in the following examples without being limited thereto:

EXAMPLE

Radioimmunoassay for Thyroxine (T-4)

A. Preparation of the Lyophilized Mixture

The following solutions were introduced, by means of a diluter-dispenser apparatus, into each of a series of polystyrene test tubes having a diameter of 12 mm and a length of 75 mm:

1. 100 microliters ($\mu$l) of a solution of $I^{125}$-T-4 [activity per 100 $\mu$l of 90 thousand counts per minute (kcpm)] including 0.25% of polyvinyl alcohol as filler and 3 mg/ml of 8-anilino-1-naphthalenesulfonic acid, ammonium salt (ANS).

2. 100 $\mu$l of aqueous solution of T-4 antiserum diluted with 0.0067 M acetic acid, to which 1 milliliter (ml) per 10 ml of an aqueous solution of 3.4 mg/ml of cupric acetate [$Cu(C_2H_3O_2)_2 \cdot H_2O$], has been added at least half an hour before the dispensing into the test tubes.

The test tubes were frozen at $-70°$ C. and thereafter immersed for a short while in liquid nitrogen. The test tubes were then lyophilized for about 15 hours and allowed to reach room temperature. Each test tube was then tightly stoppered.

B. Test Procedure

1. Manual method

25 $\mu$l of a serum sample or of an aqueous T-4 standard solution were introduced into a test tube containing the above described lyophilized mixture. The test tube was gently shaken in order to moisten all the lyophilized material with the serum sample or standard solution and to allow its complete dissolution therein. 300 $\mu$l of an aqueous tris-maleate buffer solution, pH 7.4 [prepared by dissolving 2.85 g of tris -(hydroxymethyl)aminomethane and 1.2 g of maleic acid in 290 ml of distilled water] containing 0.15% w/v of ethylenediamine tetraacetic acid (EDTA) were added to the test tube. The tube was again gently shaken in order to mix its contents.

2. Diluter-dispenser method

25 $\mu$l of the serum sample or of an aqueous T-4 standard solution and 300 $\mu$l of the above described tris-maleate buffer solution containing the EDTA were simultaneously dispensed by means of an automatic diluter-dispenser apparatus, into a test tube containing the lyophilized mixture. The test tube was gently shaken in order to dissolve the lyophilized mixture in the combined solution.

The mixture in the test tube was incubated for one hour at room temperature.

C. Separation of the Components by Ascending Chromatography

A chromatography tube (or column) packed with dry, granular cross-linked PVA (prepared as described in the aforementioned U.S. Ser. No. 852,105) was placed in the test tube and the incubation mixture was allowed to ascend in the column. After the absorption was complete, an additional amount of 500 $\mu$l of the tris-maleate buffer solution was introduced into the test tube and allowed to ascend in the column in order to complete the separation of the free T-4 from the T-4 antibody complex.

The radioactivity of the intake tip region of the column was determined by inserting the column into the well of a Thyrimeter ® gamma-counter (Ames Company Division of Miles Laboratories, Inc., Elkhart, Ind.).

The percent retention of the column was calculated using the equation:

$$\text{percent retention} = \frac{\text{partial count}}{\text{total count}} \times 100$$

where the "partial count" is the actual radioactivity of the intake tip region of the column and the "total count" is the radioactivity of the tip region of a column where no antibody was added to the reaction mixture in the test tube and, thus, the entire amount of $^{125}$I-T-4 became adsorbed at the tip region of the absorbent tube.

A standard curve was obtained by plotting the percent retention values versus the corresponding concentrations of the thyroxine standard. Typical results were as follows:

| T-4 Concentration µg/100 ml | Percent Retention |
|---|---|
| 0 | 13.49 |
| 3.0 | 19.01 |
| 6.0 | 30.67 |
| 12.0 | 60.12 |
| 18.0 | 73.61 |

Unknown amounts of T-4, in serum, can be determined in the above manner with the aid of the standard curve. Using such a standard curve, three clinical serum samples were tested, each in 20 replicates. The average results were as follows:

| | Concentration of T-4 in Serum | |
|---|---|---|
| Test Method | Expected Value* µg/100 ml | Observed value |
| Manual | 3.8 | 3.60 |
| | 8 | 8.83 |
| | 16–17 | 16.72 |
| Dilutor/Dispenser | 3.8 | 3.45 |
| | 8 | 8.32 |
| | 16–17 | 16.74 |

*As determined using "Seralute T-4⇌" assay kits manufactured by the instant assignee (U.S. Pat. No. 3,659,104)

We claim:

1. A method for preparing a dry radioimmunoassay test composition comprising a mixture of (i) a radiolabelled form of a ligand selected from haptens and antigens and (ii) an antibody for said ligand, wherein substantially all of said radiolabelled ligand is not bound to said antibody in said mixture, which method comprises the steps of:
   (a) preparing an aqueous liquid mixture of said radiolabelled ligand, said antibody, and a heavy metal cation present in an amount sufficient to inhibit substantially the complex-forming reaction between said radiolabelled ligand and said antibody, and
   (b) drying said liquid mixture.

2. The method of claim 1 wherein said heavy metal cation is cupric ion.

3. The method of claim 1 or 2 wherein said drying step is accomplished by lyophilizing said liquid mixture.

4. The method of claim 1 wherein step (a) is accomplished by preparing an aqueous solution containing said heavy metal cation and said antibody and thereafter adding to said solution said radiolabelled ligand.

5. The method of claim 1 wherein said ligand is thyroxine.

6. A dry radioimmunoassay test composition comprising a mixture of (i) a radiolabelled form of a ligand selected from haptens and antigens, (ii) an antibody for said ligand, and (iii) a heavy metal cation in an amount sufficient to inhibit substantially the complex-forming reaction between said radiolabelled ligand and said antibody.

7. The composition of claim 6 wherein said heavy metal cation is cupric ion.

8. The composition of claim 6 or 7 wherein said ligand is thyroxine.

9. A radioimmunoassay method for the determination of a ligand selected from haptens and antigens in a liquid sample, comprising the steps of:
   (a) providing a dry test composition comprising a mixture of (i) a radiolabelled form of said ligand, (ii) an antibody for said ligand, and (iii) a heavy metal cation in an amount sufficient to inhibit substantially the complex-forming reaction between said radiolabelled ligand and said antibody,
   (b) reconstituting said composition with a predetermined volume of an aqueous liquid,
   (c) combining the reconstituted liquid composition with said liquid sample and with a chelating agent for said heavy metal cation in an amount sufficient to bind substantially all of said cation present,
   (d) incubating the resulting liquid reaction mixture,
   (e) separating the fraction of said radiolabelled ligand which becomes bound to said antibody during the incubation period from that which does not become so bound, and
   (f) measuring the radioactivity of one of the separated fractions as a function of the presence or amount of said ligand in said liquid sample.

10. The method of claim 9 wherein said heavy metal cation is cupric ion.

11. The method of claim 10 wherein said chelating agent is ethylenediamine tetraacetic acid.

12. The method of claim 9 wherein in step (c) said reconstituted liquid composition is combined first with said chelating agent and thereafter with said liquid sample.

13. The method of claim 9 wherein in step (c) said reconstituted liquid composition is combined simultaneously with said liquid sample and said chelating agent.

14. The method of any of claims 9–13 wherein said ligand is thyroxine.

15. A test kit for the radioimmunoassay determination of a ligand selected from haptens and antigens in a liquid sample, comprising, in a packaged combination,
   (a) a container holding a dry test composition comprising a mixture of (i) a radiolabelled form of said ligand, (ii) an antibody for said ligand, and (iii) a heavy metal cation in an amount sufficient to inhibit substantially the complex-forming reaction between said radiolabelled ligand and said antibody, and
   (b) a container holding a chelating agent for said heavy metal cation.

16. The kit of claim 15 wherein said heavy metal cation is cupric ion.

17. The kit of claim 16 wherein said chelating agent is ethylenediamine tetraacetic acid.

18. The kit of claim 15 wherein said chelating agent is dissolved in an aqueous liquid.

19. The kit of any of claims 15–18 wherein said ligand is thyroxine.

* * * * *